United States Patent [19]
Fukui et al.

[11] Patent Number: 5,363,189
[45] Date of Patent: Nov. 8, 1994

[54] SPECTROSCOPIC ANALYSIS METHOD AND ANALYZING SYSTEM

[75] Inventors: Isao Fukui; Takao Miyama, both of Kyoto, Japan

[73] Assignee: Shimadzu Corporation, Kyoto, Japan

[21] Appl. No.: 840,526

[22] Filed: Feb. 25, 1992

[30] Foreign Application Priority Data

Feb. 28, 1991 [JP] Japan ................... 3-104909

[51] Int. Cl.⁵ .............................. G01J 3/30
[52] U.S. Cl. ...................... 356/306; 356/313; 356/318
[58] Field of Search .............. 356/306, 313, 318

[56] References Cited

U.S. PATENT DOCUMENTS

| | | | |
|---|---|---|---|
| 3,298,275 | 1/1967 | DuBois et al. | 356/313 |
| 4,140,394 | 2/1979 | Roos | 356/306 |
| 4,326,801 | 4/1982 | Ono | 356/313 |
| 4,690,558 | 9/1987 | Tsunoyama et al. | 356/318 |
| 4,898,466 | 2/1990 | Fukui et al. | 356/313 |

FOREIGN PATENT DOCUMENTS

| | | |
|---|---|---|
| 0009766 | 4/1980 | European Pat. Off. . |
| 0401470 | 12/1990 | European Pat. Off. . |
| 03138548 | 6/1991 | Japan . |

*Primary Examiner*—Vincent P. McGraw
*Assistant Examiner*—K. P. Hantis

[57] ABSTRACT

A plurality of elements in a sample are specified as monitoring elements. Each time at a exciting the sample, the light intensity of the line of the monitoring elements and the measured elements is detected and memorized. From the memorized data, the distribution for the light intensity of the line of each of the monitoring elements is determined. Based on the distribution, the preferred region for the light intensity of the line of each of the monitoring elements is defined. With reference to the memorized data, the light intensity of the line of the measured elements at every exciting in which the light intensity of the line of the monitoring elements is within the preferred region integrated.

8 Claims, 3 Drawing Sheets

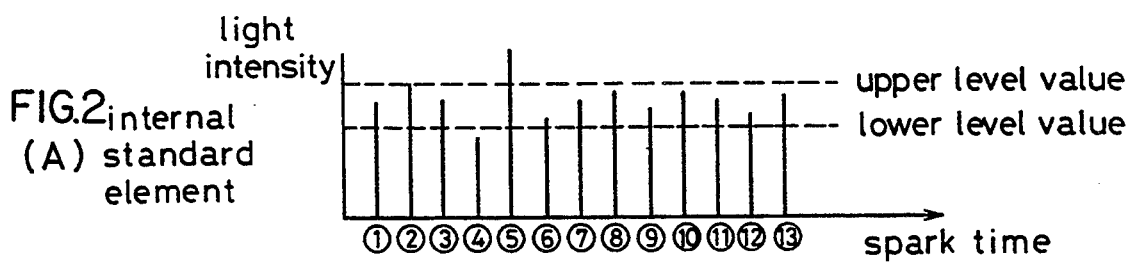
FIG. 2 (A) internal standard element
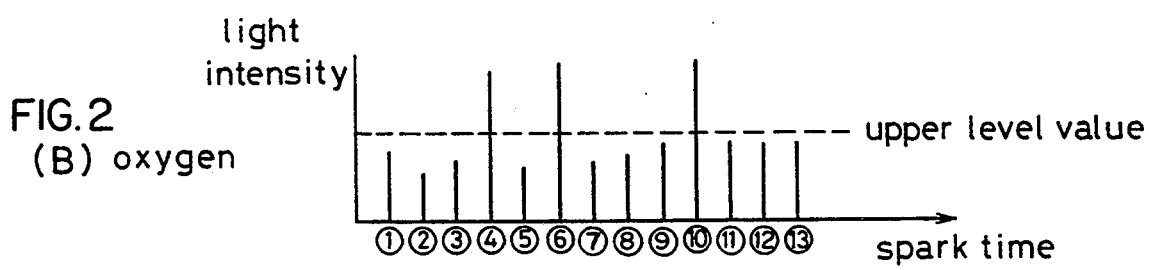
FIG. 2 (B) oxygen
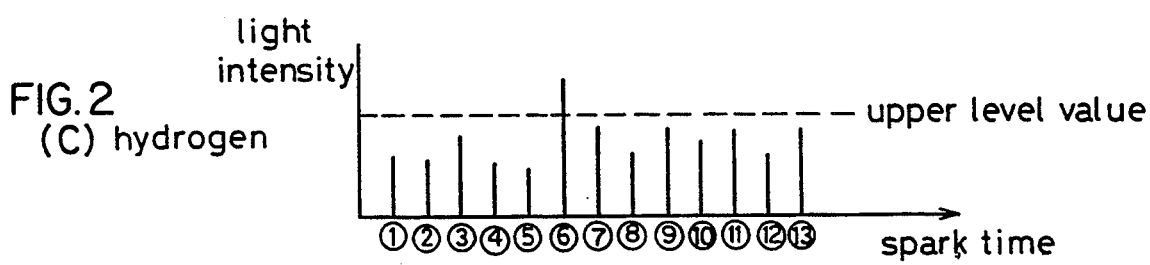
FIG. 2 (C) hydrogen
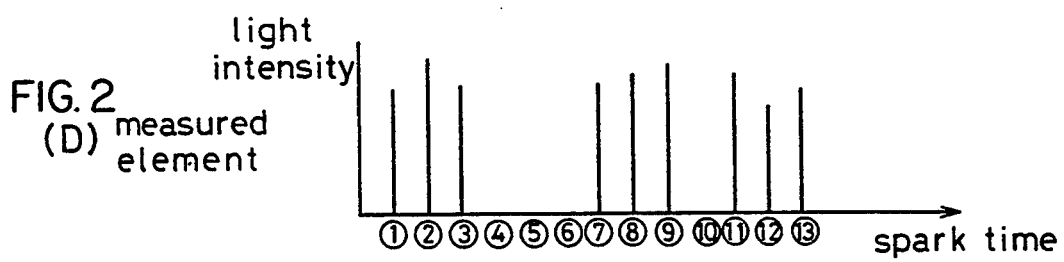
FIG. 2 (D) measured element
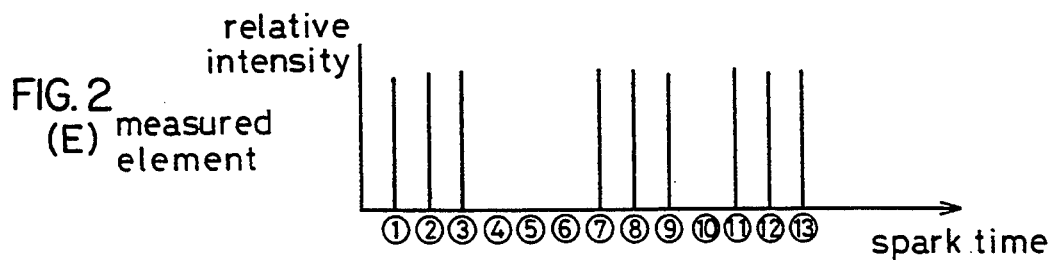
FIG. 2 (E) measured element

SPECTROSCOPIC ANALYSIS METHOD AND ANALYZING SYSTEM

BACKGROUND OF THE INVENTION

The present invention relates to a spectroscopic analysis method and system.

A spectroscopic analysis for a spark discharge is carried out such that spark discharge takes place between a discharge electrode and a specimen, and the spark is subject to spectrum analysis. The emission of the discharge is different each time the discharge is carried out. Therefore, the discharge is repeated several thousands in which the light amount of the line of each element is integrated. For quantitative analysis, a single element which is uniformly dispersed within the specimen at a predetermined amount is treated as an internal standard element. The light intensity of the line of the internal standard element is integrated. The integration of the light intensity of the line of a measured element at the time when the integration of the light amount of the line of the internal standard element reaches a predetermined amount is used as an analysis quantitative amount. However, the light amount of the spark discharge is irregular. At the discharge of which light amount is outside of the regular region, the light intensity of the line of the measured element is not always proportional with the light intensity of the line of the internal standard element. Thus, the simple integration of the measurement data of the great number cannot provide highly accurate analysis.

Conventionally, to solve the above problem, each time a single discharge happens, as far as the light intensity of the line of the internal standard element is in a certain region, the light intensity of the line of the internal standard element and the measured element is selectively integrated. However, the light intensity of the line of the internal standard element depends upon content by amount. Then, in this method, if the selective region of the light intensity of the line of the internal standard element is predetermined, the variation of the contents of the internal standard element is limited and the analysis is limited to analyzing a known specimen, disadvantageously. Although monitoring the single internal standard element may show the discharge proper, it is not sufficient to eliminate the effect of sparking of some defects such as pinholes and obstacles.

SUMMARY OF THE INVENTION

Accordingly, it is an object of the present invention to provide an improved spectroscopic analysis method and analyzing system. Briefly described, in accordance with the present invention, in spectroscopic analysis, a plurality of elements in a sample are specified as monitoring elements. Each time the sample is excited, the light intensity of the line of the monitoring elements and the measured elements is detected and memorized. From the memorized data, the distribution for the light intensity of the line of each of the monitoring elements is determined. Based on the distribution, the preferred region for the light intensity of the line of each of the monitoring elements is defined. With reference to the memorized data, the light intensity of the line of the measured elements at every excitation in which the light intensity of the line of the monitoring elements is within the preferred region is integrated.

According to the spectroscopic analyzer and analyzing method, the elements uniformly contained other than the internal standard element are defined as the monitoring elements. When the light intensity of the line of each of the plurality of monitoring elements is all within each predetermined level, the data of measured elements at this time are considered to be effective data. Ineffective data due to some defects in the specimen, poor discharge, optical dislocation and so forth can be effectively eliminated. To define the predetermined level, the analysis is repeated at a thousand to several thousands times in which the light intensity of the line of each of the plurality of monitoring elements and measured elements at each exciting is detected and memorized. Based on the memorized data, the distribution of the light intensity of the line of each of the plurality of monitoring elements is determined to set a predetermined level for each of the plurality of monitoring elements, easily and surely.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 2 shows measurement data provided by the analyzing system of FIG. 1.

DESCRIPTION OF THE PREFERRED EMBODIMENT

Figure 1:
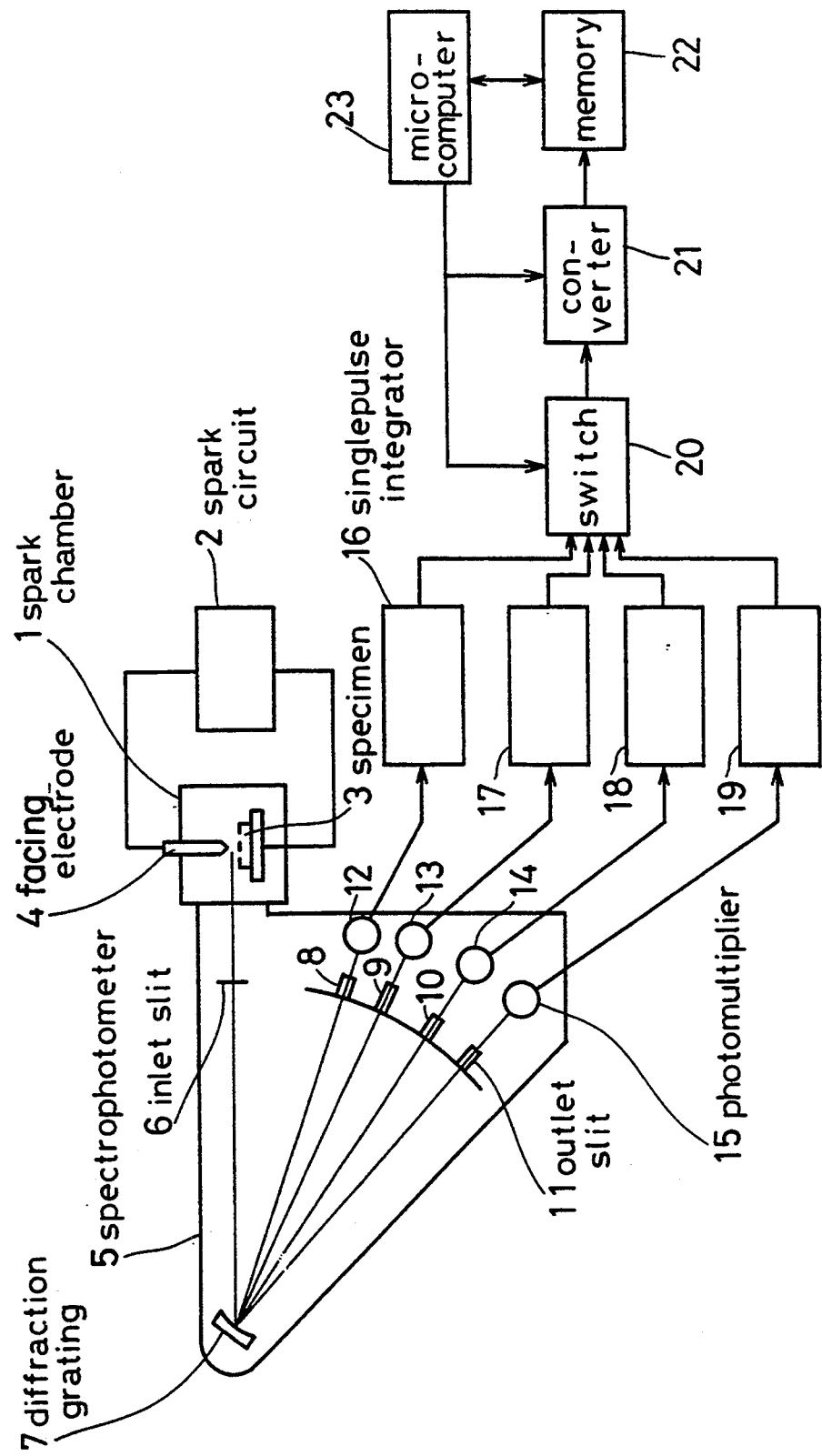
FIG. 1 shows a block diagram of a analyzing system according to a preferred embodiment of the present invention.

FIG. 1 shows a block diagram of a analyzing system according to the present invention. A spark chamber 1 is provided for sparking a specimen 3. The spark chamber 1 is full of argon gas. A spark circuit 2 is operated to generate sparking pulses. A facing electrode 4 is positioned in front of a specimen 3. A high voltage pulse is applied between the facing electrode 4 and the specimen 3 from the spark circuit 2 so that a spark discharge is generated between the facing electrode and the specimen 3. A spectrophotometer 5 is provided whose contents are located in a vacuum. An inlet slit 6 is used to take out parallel radiation from the spark discharge energy generated between the facing electrode 4 and the specimen 3. The remaining light energy is directed in a predetermined direction as shown. A diffraction grating 7 is provided for providing spectroscopic analysis and intercepts the remaining light energy. Outlet slits 8 though 11 are positioned so that the remaining light energy of the spark on the spectroscopic image plane by the diffraction grating 7 is fed to the position of the line of each of the monitoring elements. Thus, the spark energy passing through each of the outlet slits 8 through 1 only is incident on photomultipliers 12 through 15. Single pulse integrators 16 through 19 are provided for integrating the light intensity signal of the line detected by the photomultipliers 12 through 15 at the unit of each spark. A switch 20 is provided for subsequently forwarding the integration value (sample data), integrated by the integrators 16 through 19 to an analog/digital (A/D) converter 21. The A/D converter 21 is operated to transfer the received sample data to digital signals. A memory 22 is provided for storing the sample data as well as the other data. A microcomputer 23 is operated to control the respective elements and calculate measured value based on the data stored in the memory 22. The spark discharge between the specimen 3 and the facing electrode 4 is repeated at a thousand to several thousands of times to measure the light intensity for each of the monitoring elements for each spark as shown in FIG. 2(A) to FIG. 2(C). In FIG. 2, the length of the vertical bar at the same position on the time axis for each of the monitoring elements indicates the light intensity of the line for a single spark. The given light intensity data of the line of each of the monitoring elements are subsequently stored into the memory 22. From the data stored in the memory 22, the average value and the dispersion value 8 of the sample data of the monitoring elements (the internal standard elements, O, and H and so on) are determined. With reference to the dispersion conditions of the data, the effective region is then defined. For example, the effective region of the internal standard elements is set about $\pm 2\sigma$ as compared with the average. The effective region of the other monitoring elements is set lower than $\pm 2\sigma$ of the average. The reason why the excessive light intensity of the line for oxygen (O) and hydrogen (H) is excluded is that the oxide and the hydroxide maybe made of these elements to thereby make the obstacles in the specimen and the deposits of the crystalline boundary. The reason why the light intensity of these elements are large is considered to scatter the spark to the obstacles and the crystalline boundary. As far as the spark is such that the sample data of each of the monitoring elements are all contained within the effective region of the monitoring elements thus determined, the light intensity of the line of the internal standard elements and the measured elements generated for this spark are treated as the effective sample data which is extracted from the data of the memory 22, That is, when any of the sample data of the monitoring elements is outside of the effective region (the sparks ④, ⑤, ⑥ and ⑩ in FIG. 2), any measurement data at these sparks are not treated as effective measurement data. The extracted effective sample data of the measured elements and the internal standard elements are integrated. The integration of the measured elements at the time when the integrating of the internal standard elements reaches a predetermined value is outputted as measurement data. Otherwise, as shown in FIG. 2(E), the ratio of the effective sample data of the measured elements and the same data of the internal standard elements for the same spark is determined so that the average of the ratio is treated as the measured data.

Figure 3:
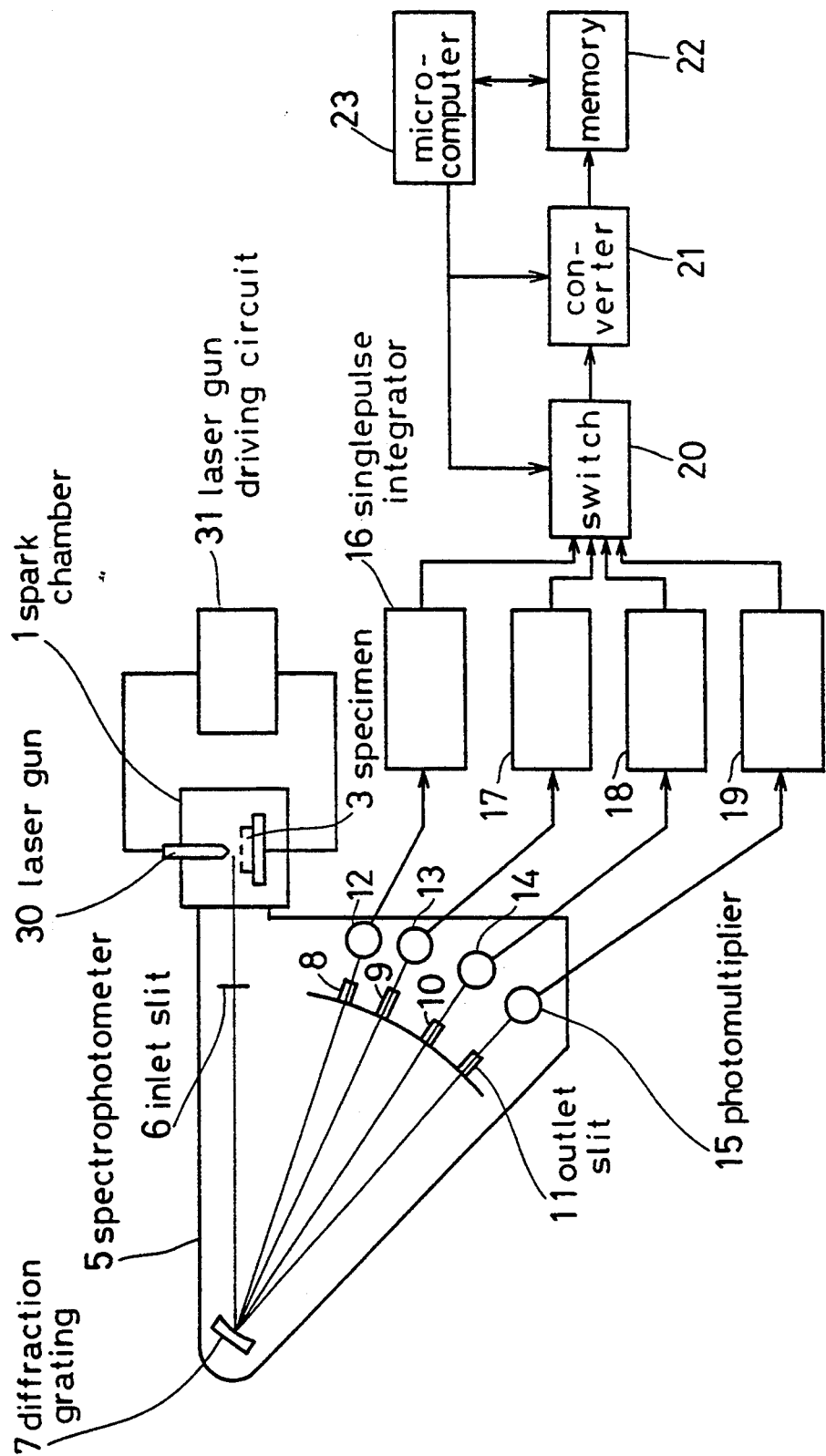
FIG. 3 shows a block diagram of a analyzing system according to another preferred embodiment of the present invention.

FIG. 3 shows another preferred embodiment in which the facing electrode 4 is replaced by the a laser gun 30 and the spark circuit 2 is replaced by the a laser gun driving circuit 31 so that the specimen 3 is excited by the laser beam. The other parts and the data processing operation are similar as the above embodiment.

The suitable laser is $N_2$ laser beam which is featured by having short laser pulse and providing high output. When the $N_2$ laser beam is incident on a metal sample under a pressure lower than several tort, the white primary plasma having a small diameter and the secondary plasma which surrounds the white primary plasma in a hemispheric form are both generated. The emission of the secondary plasma is used because the emission of the secondary plasma can provide high analysis accuracy without the influence of the background. The emission of the laser beam is expanded over the entire surface of the specimen 3 with scanning. In the above embodiment using the spark discharge, the discharge position of the spark discharge is random so that if the discharge position is shifted by a single point, it is impossible to obtain the uniform analysis results over the entire surface of the specimen 3. However, in this preferred embodiment, the emission of the laser beam is carried out with scanning over the entire surface of the specimen 3. Thus, average analysis results over the entire surface of the specimen 3 can be assured in this embodiment.

As described above, monitoring is carried out for a plurality of elements so that only the data provided for the spark when the data of all of the monitoring elements are considered proper are treated as effective. Abnormal data can be effectively eliminated to improve measurement accuracy. The predetermined level for excluding the abnormal values can be automatically set so that the predetermined level can be easily and surely set. The predetermined level is set according to the actual measurement. If iron which is an element of the stainless steel is treated as one of the internal standard element, the ratio of iron depends upon the type of stainless steel so that the average light intensity of the line of iron is also different from each other depending on the type of steel being analyzed. Even if the type of stainless steel is uncertain, a predetermined level can be automatically and preferably set. This is true in the case where oxygen and hydrogen are selected as the monitoring elements, oxygen and hydrogen being combined with the different ingredient in the different specimens and a predetermined level is set for the monitoring elements.

While only certain embodiments of the present invention have been described, it will be apparent to those skilled in the art that various changes and modifications may be made therein without departing from the spirit and scope of the present invention as claimed.

What is claimed is:

1. A spectroscopic analyzing method comprising the steps of:

exciting said specimen a predetermined number of times;

detecting the light intensity of the line of monitoring elements and measured elements each time said specimen is excited, said measured elements including ingredient elements and said monitoring elements including at least one element which comprises an internal standard element while the remaining elements comprise non-ingredient elements;

storing data of the light intensity of the line detected;

obtaining a distribution of the light intensity of the line of said monitoring elements based on said stored data;

determining an effective region of the light intensity of the line of said monitoring elements based on said distribution; and integrating the light intensity of the line of said measured elements for each excitation when the light intensity of the line of said monitoring elements is within the effective region based on said stored data.

2. The spectroscopic analyzing method as set forth in claim 1, wherein said determining step includes a step for determining an average value and a dispersion value of the light intensity of the line of said monitoring elements.

3. The spectroscopic analyzing method as set forth in claim 1, wherein said step of exciting is carried out by a spark discharge.

4. The spectroscopic analyzing method as set forth in claim 1, wherein said step of exciting is carried out by laser emission.

5. A spectroscopic analyzing system comprising:
means for exciting a specimen to cause an emission;
analyzing means for spectroscopically analyzing the emission of said specimen;
means for detecting the light intensity of predetermined lines of a spectroscopic analysis by said spectroscopic analyzing means each time said specimen is excited;
means for storing data of the light intensity of the line;
means for obtaining a distribution of the light intensity of the line of a plurality of monitoring elements defined from the data stored by said storing means;
means for determining the effective region of the light intensity of the lines of a plurality of monitoring elements based on said distribution, at least one element of said monitoring elements comprising an internal standard element while the remaining monitoring elements comprise non-ingredient elements; and
means for integrating the light intensity of the line of at least one measured element comprising an ingredient element for each excitation when the light intensity of the lines of said monitoring elements are within an effective region.

6. The spectroscopic analyzing system as set forth in claim 5, wherein said means for determining obtains a distribution of the light intensity of the line of said plurality of monitoring elements by determining the average value and the dispersion value of the light intensity of the lines of said monitoring elements.

7. The spectroscopic analyzing system as set forth in claim 5, wherein said means for exciting comprises a discharge means.

8. The spectroscopic analyzing method as set forth in claim 5, wherein said means for exciting comprises a laser emission means.

* * * * *